(12) United States Patent
Ueno

(10) Patent No.: US 8,899,751 B2
(45) Date of Patent: Dec. 2, 2014

(54) OPHTHALMIC PHOTOGRAPHING APPARATUS

(71) Applicant: Nidek Co., Ltd., Gamagori-shi, Aichi-ken (JP)

(72) Inventor: Tokio Ueno, Nagoya (JP)

(73) Assignee: Nidek Co., Ltd, Gamagori (JP)

( * ) Notice: Subject to any disclaimer, the term of this patent is extended or adjusted under 35 U.S.C. 154(b) by 0 days.

(21) Appl. No.: 13/894,961

(22) Filed: May 15, 2013

(65) Prior Publication Data

US 2013/0250237 A1 Sep. 26, 2013

Related U.S. Application Data

(63) Continuation of application No. 13/137,405, filed on Aug. 11, 2011, now Pat. No. 8,556,423, which is a continuation of application No. 12/805,847, filed on Aug. 20, 2010, now Pat. No. 8,025,402, which is a continuation of application No. 12/084,284, filed as application No. PCT/JP2006/321773 on Oct. 31, 2006, now abandoned.

(30) Foreign Application Priority Data

Oct. 31, 2005 (JP) ................................. 2005-317072

(51) Int. Cl.
- *A61B 3/14* (2006.01)
- *A61B 3/10* (2006.01)
- *G01B 9/02* (2006.01)
- *A61B 3/00* (2006.01)
- *A61B 3/12* (2006.01)

(52) U.S. Cl.
CPC ............ *A61B 3/102* (2013.01); *G01B 9/02089* (2013.01); *G01B 9/02087* (2013.01); *A61B 3/0058* (2013.01); *A61B 3/1225* (2013.01); *G01B 9/0203* (2013.01); *G01B 9/02091* (2013.01)

USPC ............ 351/206; 351/205; 351/210; 351/221

(58) Field of Classification Search
USPC ................. 351/205–206, 200–202, 210, 221; 354/62

See application file for complete search history.

(56) References Cited

U.S. PATENT DOCUMENTS

5,537,162 A 7/1996 Hellmuth et al.
5,847,806 A 12/1998 Mihashi (Continued)

FOREIGN PATENT DOCUMENTS

EP 0 697 611 A2 2/1996
EP 1 452 126 A1 9/2004

(Continued)

OTHER PUBLICATIONS

Wojtkowski, et al., "Three-dimensional Retinal Imaging with High-Speed Ultrahigh-Resolution Optical Coherence Tomography," Ophthalmology, 112, No. 10, pp. 1734-1746, Oct. 2005.

(Continued)

*Primary Examiner* — Dawayne A Pinkney
(74) *Attorney, Agent, or Firm* — Oliff PLC

(57) ABSTRACT

A method for obtaining a tomographic image of a fundus by optical coherence tomography includes the steps of setting a line, based on which the fundus tomographic image is to be obtained, on a first front image of the fundus, the first front image being a still image, establishing a positional correspondence between a second front image of the fundus and the first front image by matching the first and second front images, specifying a line on the second front image based on positional information on the line set on the first front image, and the established positional correspondence, and obtaining the fundus tomographic image that corresponds to the lines on the first and second front images by scanning measurement light with the use of an optical scanner provided to an interference optical system.

5 Claims, 5 Drawing Sheets

(56) References Cited

U.S. PATENT DOCUMENTS

| | | | |
|---|---|---|---|
| 5,975,697 A | 11/1999 | Podoleanu et al. | |
| 6,377,349 B1 | 4/2002 | Fercher | |
| 6,668,185 B2 | 12/2003 | Toida | |
| 7,506,978 B2 * | 3/2009 | Nanjo | 351/204 |
| 2002/0051512 A1 | 5/2002 | Toida et al. | |
| 2002/0127010 A1 | 9/2002 | Ohtsuka | |
| 2003/0053072 A1 | 3/2003 | Fercher et al. | |
| 2004/0114151 A1 | 6/2004 | Tanno et al. | |
| 2004/0260183 A1 | 12/2004 | Lambert et al. | |
| 2005/0190371 A1 | 9/2005 | Knuttel | |
| 2007/0070295 A1 | 3/2007 | Tsukada et al. | |

FOREIGN PATENT DOCUMENTS

| | | |
|---|---|---|
| JP | A-06-511312 | 12/1994 |
| JP | A 10-33484 | 2/1998 |
| JP | A 11-253403 | 9/1999 |
| JP | A-2002-306415 | 10/2002 |
| JP | A 2002-310899 | 10/2002 |
| JP | A 2003-543 | 1/2003 |
| JP | A 2004-28970 | 1/2004 |
| JP | A 2005-518535 | 6/2005 |
| JP | WO 2006/022045 A1 | 3/2006 |
| JP | WO2007052670 * | 5/2007 |
| WO | WO 92/19930 | 11/1992 |
| WO | WO 2004/071286 A1 | 8/2004 |

OTHER PUBLICATIONS

Jiao, et al., "Simultaneous acquisition of sectional and fundus ophthalmic images with spectral-domain optical coherence tomography," Optics Express, 13, No. 2, pp. 444-452, Jan. 24, 2005.

Oct. 26, 2012 Office Action issued in U.S. Appl. No. 13/137,405.

* cited by examiner

OPHTHALMIC PHOTOGRAPHING APPARATUS

This is a Continuation of application Ser. No. 13/137,405 filed Aug. 11, 2011, which in turn is a Continuation of application Ser. No. 12/805,847 filed Aug. 20, 2010, which is a Continuation of application Ser. No. 12/084,284 filed Jun. 3, 2008, which is a U.S. National Phase of International Application No, PCT/JP2006/321773 filed Oct. 31, 2006. The disclosure of the prior applications are hereby incorporated by reference herein in its entirety.

TECHNICAL FIELD

The present invention relates to an ophthalmic photographing apparatus for obtaining a tomographic image of a fundus.

BACKGROUND ART

Conventionally, there is known a method to noninvasively obtain a tomographic (cross-sectional) image of a fundus by optical coherence tomography (OCT) using low coherent light. In addition, a multifunction ophthalmic photographing apparatus is proposed, in which an optical system of an OCT apparatus which obtains the tomographic image of the fundus by OCT, and an optical system of a fundus camera (FC) which is conventionally used and obtains a front (surface) image of the fundus, are combined (see U.S. Pat. No. 5,847,806 corresponding to Japanese Patent Application Unexamined Publication No. Hei10-33484).

However, the ophthalmic photographing apparatus currently proposed obtains the tomographic image and the front image independently, and therefore it is difficult to know to which position on the front image the tomographic image corresponds (where on the front image a measurement (photographing) position of the tomographic image is).

DISCLOSURE OF THE INVENTION

Problem to be Solved by the Invention

An object of the invention is to provide an ophthalmic photographing apparatus capable of checking a measurement (photographing) position of a tomographic (cross-sectional) image of a fundus on a front (surface) image of the fundus.

Means for Solving the Problems

To solve the above problems, the present invention is characterized as having configurations described below.

(1) An ophthalmic photographing apparatus includes a first optical system for obtaining a tomographic image of a fundus by optical coherence tomography using low coherent light, a second optical system for obtaining a visible front image of the fundus, a third optical system for obtaining an infrared front image of the fundus, a monitor, setting means which sets a line for obtaining a two-dimensional tomographic image of the fundus on the infrared front image displayed on the monitor, and control means which establishes a positional correspondence between the infrared front image on which the line is set and the visible front image and displays a line on the visible front image displayed on the monitor.

(2) The ophthalmic photographing apparatus according to (1), wherein the control means establishes the positional correspondence between the infrared front image and the visible front image by extracting characteristic points in the infrared front image and the visible front image and matching the characteristic points by image processing.

(3) The ophthalmic photographing apparatus according to (1), wherein the first optical system includes scanning means which performs two-dimensional scanning of measurement light with respect to the fundus, and optical path changing means which changes an optical path length of reference light in synchronization with the scanning of the measurement light by the scanning means.

(4) The ophthalmic photographing apparatus according to (3), wherein the first optical system also serves as the third optical system and obtains a three-dimensional tomographic image and the infrared front image of the fundus.

(5) The ophthalmic photographing apparatus according to (1), wherein the third optical system includes an image-pickup element which measurement light of the first optical system enters.

(6) An ophthalmic photographing apparatus includes a first optical system for obtaining a three-dimensional tomographic image of a fundus by optical coherence tomography using low coherent light, a second optical system for obtaining a visible front image of the fundus, a monitor, setting means which sets a line for obtaining a two-dimensional tomographic image of the fundus on the visible front image displayed on the monitor, and control means which obtains the two-dimensional tomographic image from the three-dimensional tomographic image based on the set line and displays the two-dimensional tomographic image on the monitor.

(7) The ophthalmic photographing apparatus according to (6), wherein the control means establishes a positional correspondence between the visible front image and the three-dimensional tomographic image by extracting characteristic points in the visible front image and the three-dimensional tomographic image and matching the characteristic points by image processing.

(8) The ophthalmic photographing apparatus according to (6), wherein the first optical system includes scanning means which performs two-dimensional scanning of measurement light with respect to the fundus, and optical path changing means which changes an optical path length of reference light in synchronization with the scanning of the measurement light by the scanning means.

BEST MODE FOR CARRYING OUT THE INVENTION

Figure 1:
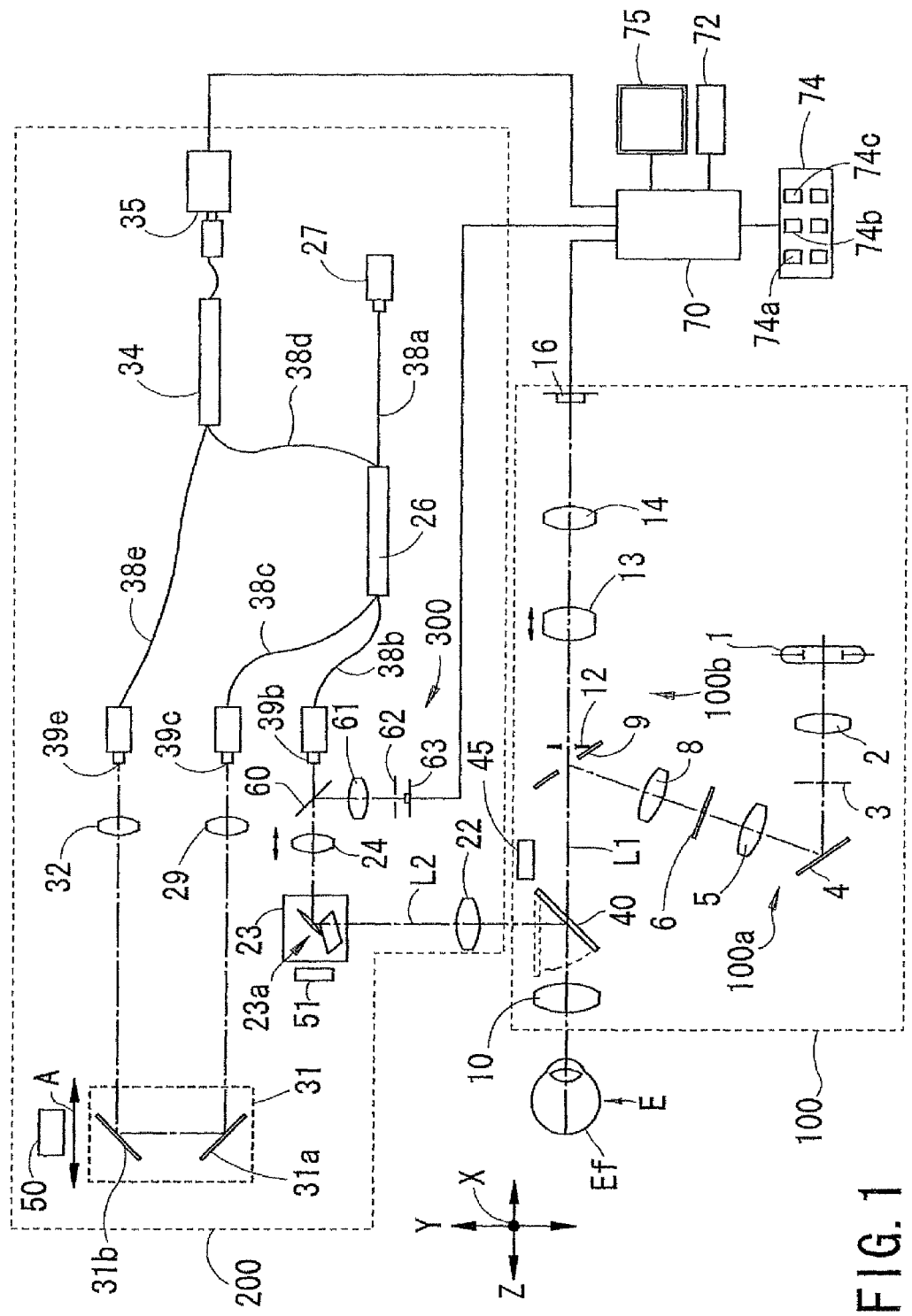
FIG. 1 is a view showing a schematic configuration of an optical system and a control system of an ophthalmic photographing apparatus according to a preferred embodiment of the present invention.

A detailed description of one preferred embodiment of the present invention is provided below with reference to the accompanying drawings. FIG. 1 is a view showing a schematic configuration of an optical system and a control system of an ophthalmic photographing apparatus according to a preferred embodiment of the present invention. In the preferred embodiment, a depth direction of an examinee's eye is referred to as a Z-direction, a horizontal direction perpendicular to the depth direction is referred to as an X-direction, and a vertical direction perpendicular to the depth direction is referred to as a Y-direction.

The optical system of the ophthalmic photographing apparatus includes a fundus camera (FC) optical system 100 for obtaining a visible (color) front (surface) image of a fundus Ef of an examinee's eye E, an optical coherence tomography (OCT) optical system 200 for obtaining an infrared (monochrome) tomographic (cross-sectional) image of the fundus Ef, and a scanning laser ophthalmoscope (SCL) optical system 300 for obtaining an infrared (monochrome) front (surface) image of the fundus Ef.

An illumination optical system 100a of the FC optical system 100 includes a visible light source 1 for photographing such as a flash light, a condenser lens 2, a ring slit plate 3, a total reflection mirror 4, a relay lens 5, a black dot plate 6 having a black dot at its center, a relay lens 8, a hole mirror 9, and an objective lens 10.

A photographing optical system 100b of the FC optical system 100 includes the objective lens 10, the hole mirror 9, a diaphragm 12, a focusing lens 13 movable in a direction of an optical axis, an image forming lens 14, and a two-dimensional image-pickup element 16 for photographing which has sensitivity to a visible range.

A visible light from the light source 1 illuminates the fundus Ef via the condenser lens 2 to the objective lens 10, and the visible light reflected from the fundus Ef forms a front image of the fundus Ef on the image-pickup element 16 via the objective lens 10 to the image forming lens 14.

Incidentally, since a known optical system of a fundus camera can be used as the FC optical system 100 (the illumination optical system 100a and the photographing optical system 100b), detailed descriptions of the FC optical system 100 are omitted herein.

An output signal from the image-pickup element 16 is inputted into a calculation control unit 70. The calculation control unit 70 stores an image obtained by the image-pickup element 16 in a memory 72. In addition, the calculation control unit 70 is connected with a monitor 75 and controls image display on the monitor 75.

Between the objective lens 10 and the hole mirror 9, a dichroic mirror 40 for making an optical axis L1 of the FC optical system 100 and an optical axis L2 of the OCT optical system 200 and the SLO optical system 300 coaxial is arranged such that the dichroic mirror 40 can be flipped up by a driving mechanism unit 45. The dichroic mirror 40 has a property of reflecting infrared measurement light of the OCT optical system 200 and infrared measurement light of the SLO optical system 300 and transmitting the other light.

The OCT optical system 200 provided on the opposite side of the dichroic mirror 40 is described below. An infrared light source 27 for measurement (photographing) such as a super luminescent diode (SLID) is a light source which emits low coherent light used as measurement light (photographing light, object light) and reference light, for example, a light source having a band of 50 nm with a center wavelength of 840 nm (a range with wavelengths of 815 to 865 nm). Infrared light from the light source 27 passes through an optical fiber 38a being a light guide, and enters a fiber coupler 26 being a light-dividing member to be divided into the measurement light and the reference light.

On an optical path of the measurement light from the fiber coupler 26 to the fundus Ef, arranged are an optical fiber 38b being a light guide, a relay lens 24 movable in a direction of an optical axis in accordance with refractive power of the eye E, a scanning unit 23, a relay lens 22, the dichroic mirror 40, and the objective lens 10. On an optical path of the measurement light from the fundus Ef to a photodetector 35, arranged are the objective lens 10 to the fiber coupler 26, an optical fiber 38d being a light guide, and a fiber coupler 34 being a light-coupling member. An end 39b of the optical fiber 38b is arranged in a position conjugate with the fundus Ef. The scanning unit 23 includes a pair of galvano mirrors 23a, which are made swingable (rotatable) by a driving mechanism unit 51 to scan the measurement light in the X- and/or Y-directions. In addition, reflective surfaces of the galvano mirrors 23a are arranged in positions conjugate with a pupil of the eye E (in the preferred embodiment, arranged to have a conjugate positional relationship between an intermediate position of the galvano mirrors 23a and the pupil).

The measurement light exiting from the fiber end 39b passes through the relay lens 24, is reflected by the galvano mirrors 23a, passes through the relay lens 22, is reflected by the dichroic mirror 40, passes through the objective lens 10, and converges at the fundus Ef. The measurement light reflected from the fundus Ef enters the fiber end 39b via the objective lens 10 to the relay lens 24, passes through the optical fiber 38b, the fiber coupler 26 and the optical fiber 38d, and enters the fiber coupler 34.

On the other hand, on an optical path of the reference light from the fiber coupler 26 to the photodetector 35, arranged are an optical fiber 38c being a light guide, a collimator lens 29, an optical path length changing unit 31, a condenser lens 32, an optical fiber 38e being a light guide, and the fiber coupler 34. The optical path length changing unit 31 includes total reflection mirrors 31a and 31b, and is movable in a direction of the optical axis (in a direction of an arrow A) by a driving mechanism unit 50 to change an optical path length of the reference light.

The reference light exiting from an end 39c of the optical fiber 38c passes through the collimator lens 29, is reflected by the total reflection mirrors 31a and 31b, passes through the condenser lens 32, enters an end 39e of the optical fiber 38e, passes through the optical fiber 38e, and enters the fiber coupler 34.

The measurement light and the reference light entering the fiber coupler 34 are synthesized and photo-received (detected) on the photodetector 35, and based on an interference phenomenon when an optical path length of the measurement light reflected by layers of the fundus Ef is equal to the optical path length of the reference light changed by the optical path length changing unit 31, intensity distribution of the reflected measurement light in the Z-direction is obtained (in the preferred embodiment, this method is referred to as an A-scan (linear scanning)). In addition, by scanning of the measurement light in the X- or Y-direction and the change of the optical path length of the reference light, a two-dimensional tomographic image in an X-Z plane or a Y-Z plane of the fundus Ef is obtained (in the preferred embodiment, this method is referred to as a s-scan (longitudinal scanning)). In addition, by the scanning of the measurement light in the X- and Y-directions, a two-dimensional tomographic image in an X-Y plane of the fundus Ef is obtained (in the preferred embodiment, this method is referred to as a C-scan (transversal scanning)). Further, by making use of these methods, a three-dimensional tomographic image of the fundus Ef is obtained. In other words, by the scanning of the measurement light in the X- and Y-directions and the change of the optical path length of the reference light, the three-dimensional tomographic image of the fundus Ef is obtained.

In the A-scan, a position (a portion) where high intensity is first obtained is a surface (surface layer) of the fundus Ef. Accordingly, a surface (surface layer) image of the fundus Ef is obtained by connecting positions (portions) where high intensity is first obtained in the A-scan with the scanning of the measurement light in the X- and Y-directions.

The SLO optical system 300 is described below. The SLO optical system 300 in the preferred embodiment shares the light source 27, the optical fibers 38a and 38b, the scanning unit 23, the dichroic mirror 40, the objective lens 10, and others with the OCT optical system 200. In addition, a half mirror 60 is arranged between the fiber end 39b and the relay lens 24, and in a reflection direction of the half mirror 60, arranged are a condenser lens 61 and an aperture 62 configurating a confocal optical system, and a photodetector 63. The aperture 62 is arranged in a position conjugate with the fundus Ef. According to such a configuration, the infrared measurement light from the light source 27 is scanned in the X- and Y-directions by the scanning unit 23, and the measurement light reflected from a position (a portion) of the fundus Ef conjugate with the aperture 62 is photo-received on the photodetector 63 to obtain a front image of the fundus Ef.

An operation of the ophthalmic photographing apparatus having the above-mentioned configuration is described below.

When an anterior-segment image of the eye E obtained by an unillustrated anterior-segment observation optical system is displayed on the monitor 75, alignment of the ophthalmic photographing apparatus (the optical system) with respect to the eye E is performed so that an infrared front image of the fundus Ef obtained by the SLO optical system 300 is displayed on the monitor 75. When the infrared front image is displayed on the monitor 75 (see FIG. 2), focusing of the ophthalmic photographing apparatus (the optical system) is performed on the fundus Ef so as to clearly display the infrared front image.

Then, a step to obtain a two-dimensional tomographic image of the fundus Ef by the OCT optical system 200 is performed. In the preferred embodiment, a case where the two-dimensional tomographic image in the X-Z plane is obtained by the B-scan is described.

First, a measurement position of the tomographic image to be obtained is set by an examiner on an SLO image displayed on the monitor 75 in real time. A measurement (photographing) position of the two-dimensional tomographic image in the X- or Y-directions is set based on the infrared front image displayed on the monitor 75. By operating a setting switch 74a of a switch unit 74 connected to the calculation control unit 70, a line P1 (see FIG. 2) indicating the measurement position, which is electrically displayed on the infrared front image, is moved, and the measurement position is set. The tomographic image in the X-Z plane is obtained when the line P1 is set to be horizontal, while the tomographic image in the Y-Z plane is obtained when the line P1 is set to be vertical. In addition to the straight form, the line P1 may be set to have an arbitrary form such as a curved form.

In addition, a measurement position of the two-dimensional tomographic image in the Z-direction is set based on a scanning width (e.g. 3 mm) and a scanning step of the measurement light in the Z-direction. For example, when the scanning width is set to 3 mm and the scanning step is set to 10 μm, the two-dimensional tomographic image having a depth of 3 mm and a step of 10 μm is obtained.

When a trigger switch 74b of the switch unit 74 is operated, the calculation control unit 70 starts measurement (photographing) of the two-dimensional tomographic image in the X-Z plane by the B-scan based on the set measurement position. More specifically, the calculation control unit 70 controls the scanning unit 23 to scan the measurement light based on a display position of the line P1 set on the infrared front image so as to obtain the two-dimensional tomographic image corresponding to the position and the length of the line P1. Since a relationship between the display position (a position on the monitor) of the line PI and a scanning position of the measurement light by the scanning unit 23 is predetermined, the calculation control unit 70 controls the driving mechanism unit 51 to scan the measurement light with respect to the scanning position and a scanning range corresponding to the display position and the length of the set line P1. In addition, the calculation control unit 70 stores the infrared front image obtained at the start of the measurement of the two-dimensional tomographic image in the memory 72.

The calculation control unit 70 controls the driving mechanism unit 51 so that the scanning unit 23 scans the measurement light in the X-direction, and controls the driving mechanism unit 50 so that the optical path length changing unit 31 changes the optical path length of the reference light based on the set scanning width and the scanning step.

Figure 3:
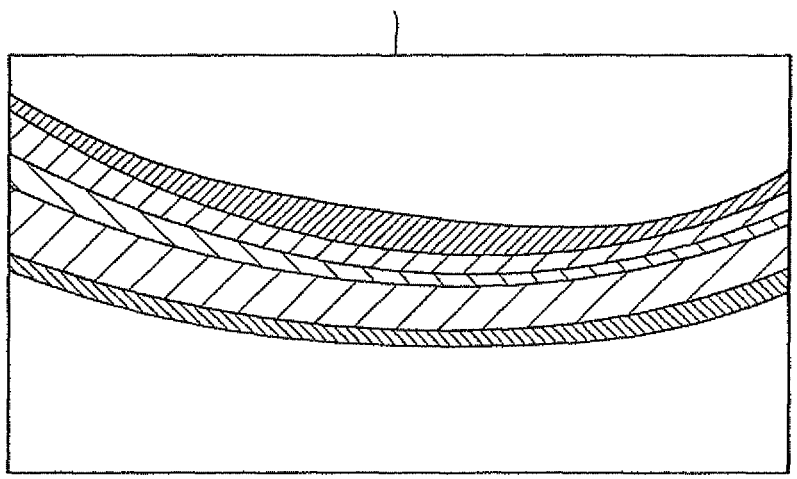
FIG. 3 is a view showing a display example of the two-dimensional tomographic image of the fundus.

The photodetector 35 sequentially detects interference light obtained by synthesizing the measurement light reflected from the fundus Ef and the reference light, and the calculation control unit 70 obtains intensity distribution of the reflected measurement light in the X- and Z-directions. When the optical path length of the reference light reaches the set scanning width, the measurement is terminated. The calculation control unit 70 then constructs the two-dimensional tomographic image in the X-Z plane using known image processing techniques based on the obtained intensity distribution of the reflected measurement light in the X- and Z-directions, and displays it on the monitor 75 (see FIG. 3).

When the two-dimensional tomographic image in the set measurement position is displayed on the monitor 75, a step to obtain the visible front image of the fundus Ef by the FC optical system 100 is then performed. When alignment and focusing are performed while observing the infrared front image displayed on the monitor 75 and a trigger switch 74c of the switch unit 74 is operated, the calculation control unit 70 controls the driving mechanism unit 45 to remove (flip up) the dichroic mirror 40 from the optical path and lights the light source 1.

The visible light from the light source 1 illuminates the fundus Ef, and the visible light reflected from the fundus Ef forms the front image of the fundus Ef on the image-pickup element 16. The calculation control unit 70 stores the obtained visible front image of the fundus Ef (see FIG. 2) in the memory 72.

Figure 2:
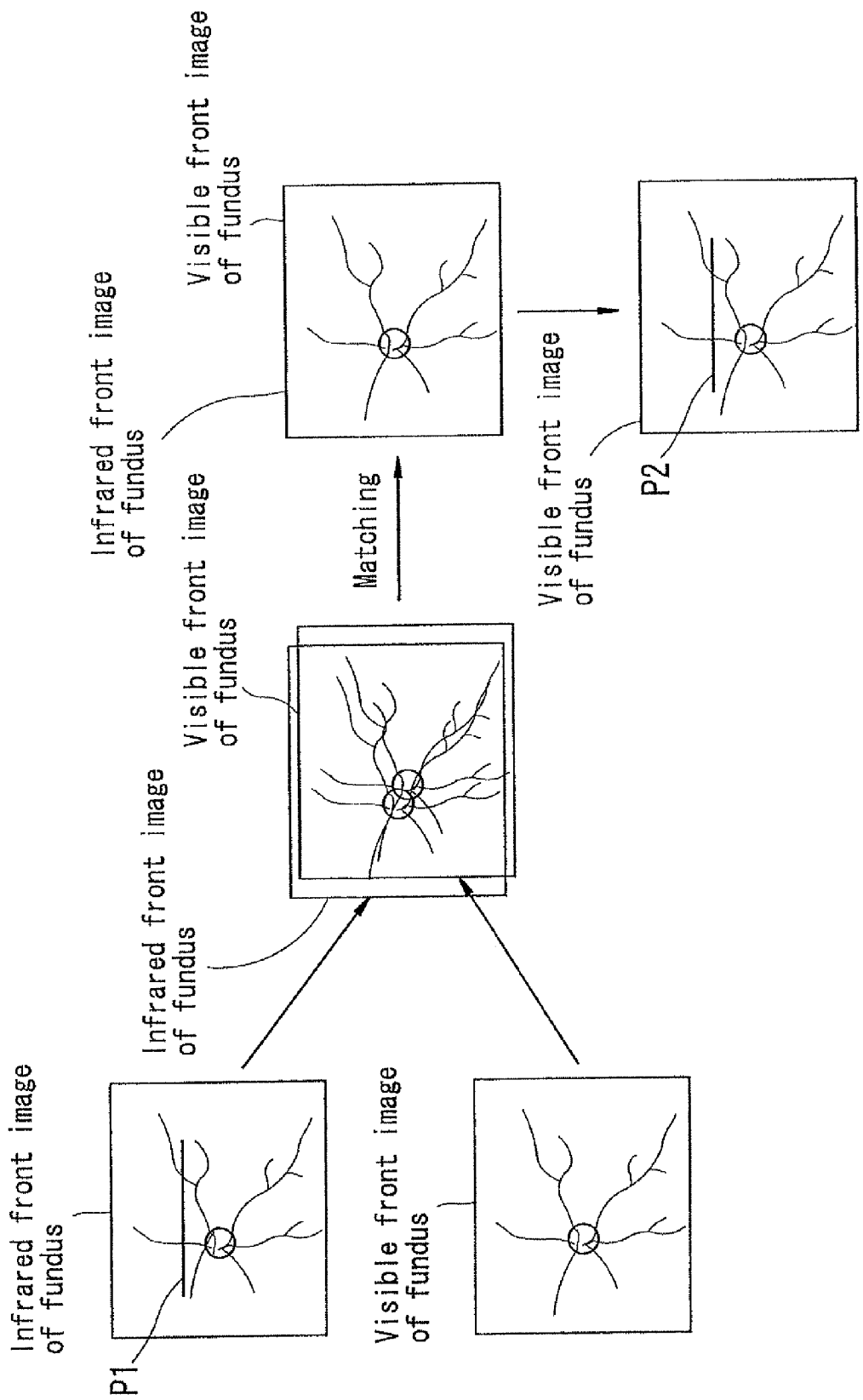
FIG. 2 is a view showing display examples of an infrared front image of a fundus and a visible front image of the fundus, a display example of a line indicating a measurement (photographing) position of a two-dimensional tomographic image of the fundus, and a positional correspondence between the infrared front image and the visible front image.

The calculation control unit 70 extracts characteristic points, such as blood vessels and optic papillae, in the infrared front image and the visible front image stored in the memory 72 and matches them by image processing, thereby establishing a positional correspondence between the infrared front image and the visible front image (FIG. 2).

When the positional correspondence between the infrared front image and the visible front image is established, the calculation control unit 70 specifies the measurement position of the two-dimensional tomographic image on the infrared front image based on the display position of the line P1 on the infrared front image. Then, the calculation control unit 70 specifies the measurement position of the two-dimensional tomographic image on the visible front image based on the correspondence between the infrared front image and the visible front image, displays the visible front image on the monitor 75, and electrically displays a line P2 indicating the specified measurement position of the two-dimensional tomographic image on the visible front image (see FIG. 2). Accordingly, the measurement position of the two-dimensional tomographic image in the X-Z plane obtained by the B-scan can be checked on the visible front image, enabling precise understanding of the correspondence between the two-dimensional tomographic image and the visible front image having an excellent resolution and a contrast.

By the foregoing manner, it is also possible to set the measurement position of the two-dimensional tomographic image on the visible front image. In this case, when the measurement position of the two-dimensional tomographic image is set on the visible front image displayed on the monitor 75, the calculation control unit 70 establishes a positional correspondence between the visible front image and the infrared front image and specifies the measurement position of the two-dimensional tomographic image on the infrared front image. Then, the calculation control unit 70 controls the scanning unit 23 to scan the measurement light based on the specified measurement position. Accordingly, the two-dimensional tomographic image can be obtained based on the measurement position which is set on the visible front image.

Incidentally, in the preferred embodiment, the infrared front image is obtained by the SLO optical system 300; however, the present invention is not limited thereto, and any systems capable of obtaining a front (surface) image of the fundus Ef by infrared light may be used. In the preferred embodiment. the line for obtaining the tomographic image is set on the SLO image of the fundus; however. the present invention is not limited thereto, and the line may be set based on any observation image obtained with the use of an observation optical system for illuminating and observing the fundus of the examinee's eye by infrared light. For example, an infrared fundus image that is obtained by illuminating the entire region of the fundus of the examinee's eye with infrared light and by detecting reflected light from the fundus by a two-dimensional photographic element or an OCT fundus image that is obtained by using OCT optical system 200 also as an observation optical system may be used as a fundus observation image.

The observation images obtained from the three-dimensional tomographic image for establishing a correspondence to the visible front image include images such as a surface image and a two-dimensional tomographic image in the X-Y plane in a predetermined position in the Z-direction. The observation images also include a sum of the interference signals from different depths obtained at each measurement position in the X-Y plane.

Figure 4:
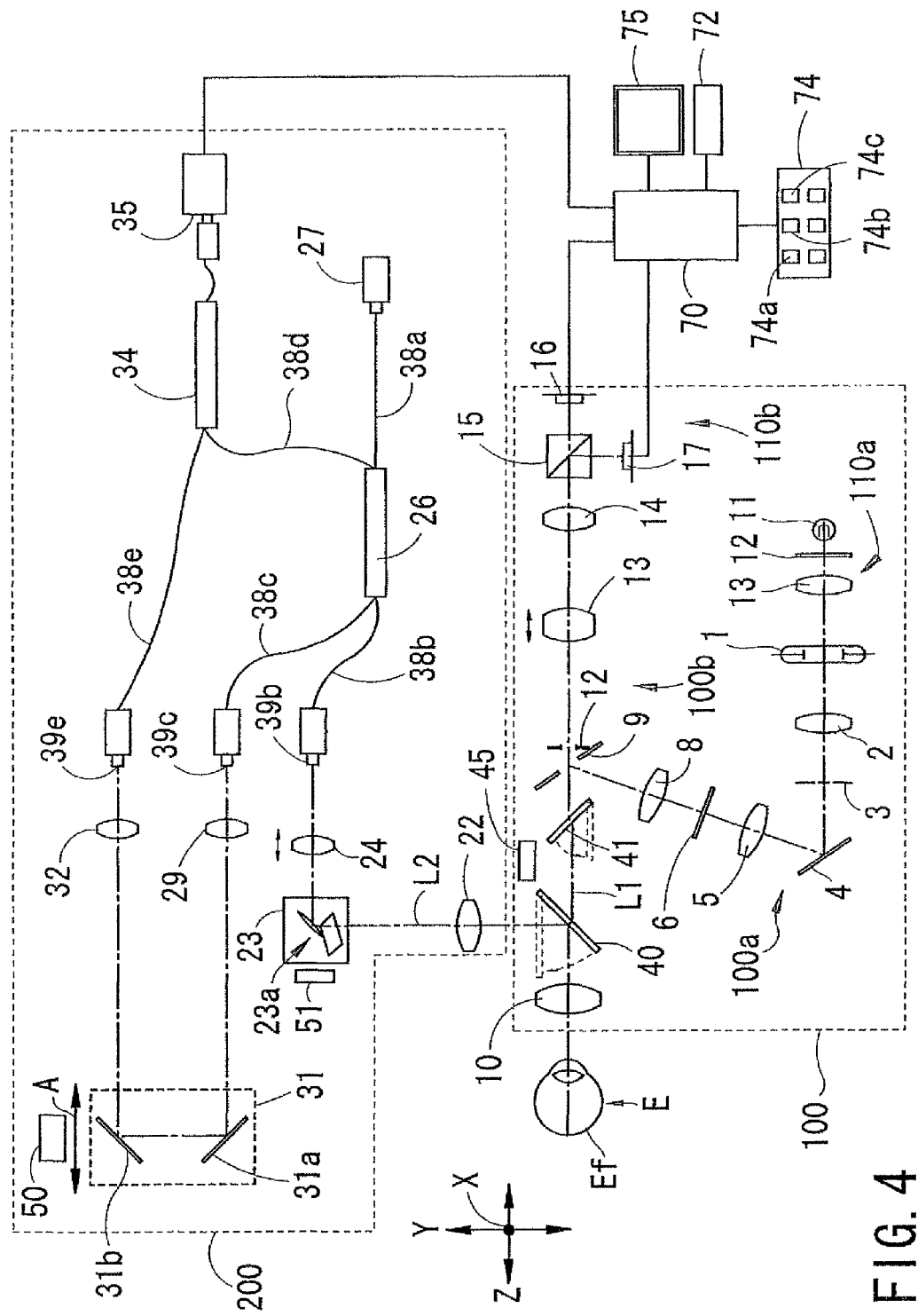
FIG. 4 is a view showing a schematic configuration of a modified embodiment of the optical system of the ophthalmic photographing apparatus.

An example in which an optical system for obtaining the infrared front image of the fundus Ef is provided in the FC optical system 100 is described below. FIG. 4 is a view showing a schematic configuration of a modified embodiment of the optical system of the ophthalmic photographing apparatus. In addition to the illumination optical system 100a and the photographing optical system 100b for obtaining the visible front image of the fundus Ef, an illumination optical system 110a and a photographing optical system 110b for obtaining the infrared front image of the fundus Ef are arranged in the FC optical system 100 in FIG. 4. The illumination optical system 110a includes a light source 11 for observation such as a halogen light, a filter 12 having a property of filtering out a range with wavelengths of 815 to 865 nm and transmits a range with wavelengths of 700 to 815 nm and a range with wavelengths of more than 865 nm, a condenser lens 13, and the condenser lens 2 to the objective lens 10 which are shared with the illumination optical system 100a. The photographing optical system 110b includes the objective lens 10 to the image forming lens 14 which are shared with the photographing optical system 100b, a dichroic mirror 15 having a property of reflecting infrared light and a part of visible light and transmitting most of the visible light, and a two-dimensional image-pickup element 17 for observation having sensitivity to an infrared range, which is arranged on the reflection side of the dichroic mirror 15. Additionally, on the image-pickup element 16 side of the dichroic mirror 40, a glass plate 41 which corrects a deviation of the optical axis L1 caused by the dichroic mirror 40 is arranged such that the glass plate 41 can be flipped up by the driving mechanism unit 45.

Light from the light source 11 is made into infrared light by the filter 12 and illuminates the fundus Ef via the condenser lens 13 to the objective lens 10. The infrared light reflected from the fundus Ef forms the front image of the fundus Ef on the image-pickup element 17 via the objective lens 10 to the dichroic mirror 15. An output signal from the image-pickup element 17 is inputted into the calculation control unit 70.

In this example, the dichroic mirror 40 has a property of reflecting most of the infrared measurement light of the OCT optical system 200 and transmitting a part thereof, and a part of the infrared measurement light enters the image-pickup element 17, thereby enabling visual observation of a scanning line of the measurement light on the infrared front image displayed on the monitor 75.

The measurement (photographing) position of the two-dimensional tomographic image in the X- and Y-directions is set based on the infrared front image displayed on the monitor 75. In this case, the measurement position of the two-dimensional tomographic image is set by moving the scanning line of the measurement light, which is visually observed, without displaying the line 21 as in the case of the foregoing example.

When the trigger switch 74b is operated, the calculation control unit 70 starts measurement (photographing) of the two-dimensional tomographic image in the X-Z plane by the B-scan based on the scanning line of the measurement light at the time. Since the measurement light has already been scanned in the X-direction, it is sufficient only to change the optical path length of the reference light by the optical path length changing unit 31. In addition, the calculation control unit 70 stores the infrared front image obtained at the start of the measurement of the two-dimensional tomographic image. When the two-dimensional tomographic image is obtained as above, the visible front image is then obtained.

When the two-dimensional tomographic image and the visible front image are obtained, the calculation control unit 70 extracts characteristic points in the infrared front image and the visible front image stored in the memory 72 and matches them by image processing, thereby establishing a positional correspondence between the infrared front image and the visible front image.

Then, the calculation control unit 70 extracts a scanning line portion of the measurement light on the infrared front image (for example, straight image signals having a luminance level within a fixed range may be extracted from the whole image) and synthesizes and displays the scanning line portion in the same position on the visible front image. Accordingly, the measurement position of the two-dimensional tomographic image in the X-Z plane obtained by the B-scan can be checked on the visible front image, enabling precise understanding of the correspondence between the two-dimensional tomographic image and the visible front image having an excellent resolution and a contrast.

Figure 5:
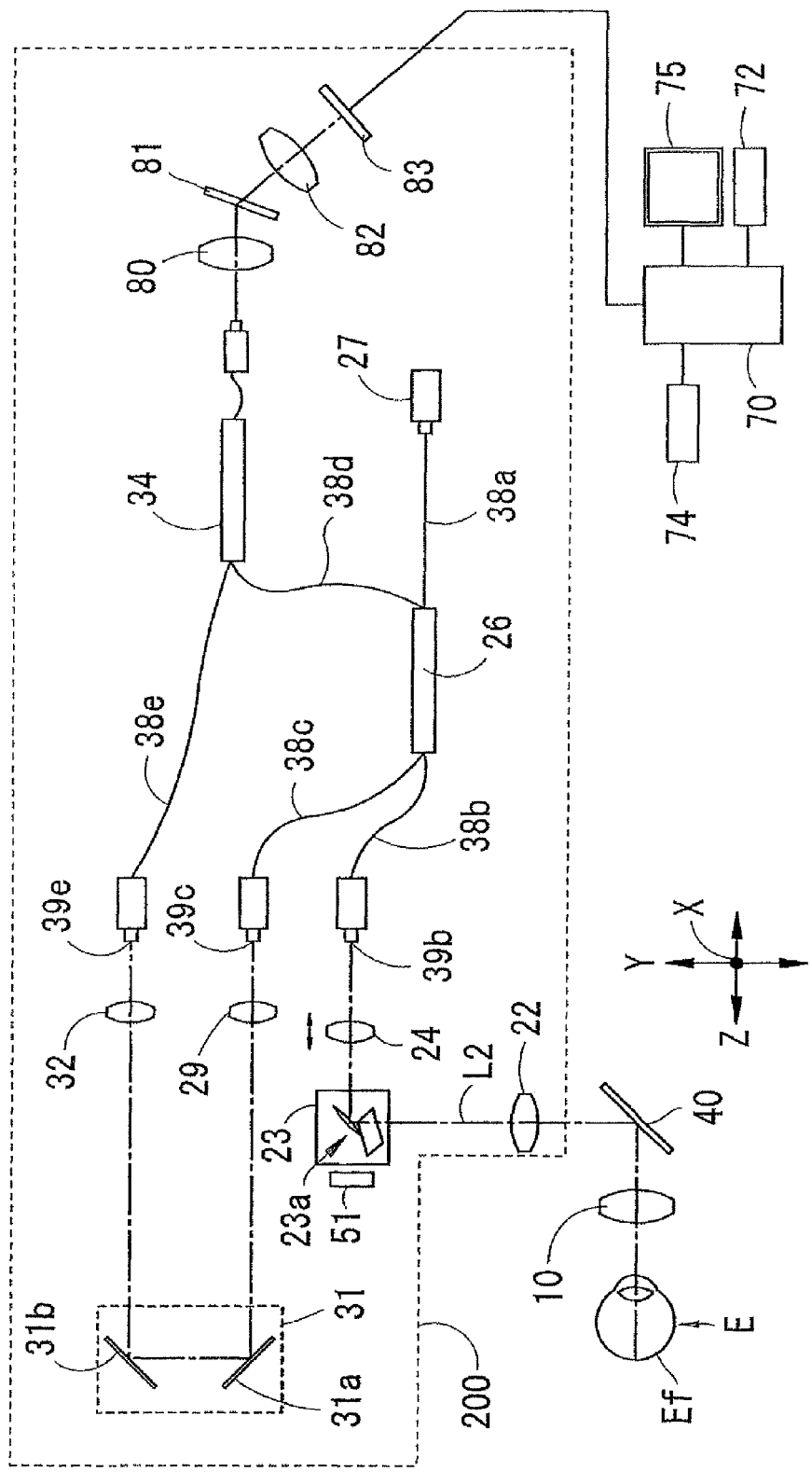
FIG. 5 is a view showing a schematic configuration of a modified embodiment of the optical system of the ophthalmic photographing apparatus.

In the foregoing description, time domain OCT (TD-OCT) is described which obtains a tomographic image by moving the optical path length changing unit 31 and changing the optical path length of the reference light; however, it is not limited thereto, and the tomographic image may be obtained by other measurement principle. For example, spectral domain OCT (SD-OCT) using Fourier transform may be used. A configuration of the SD-OCT is briefly described below referring to FIG. 5. Incidentally, configurations of portions other than those described below are omitted since the same configurations as those of the OCT optical system 200 in FIG. 1 can be used.

The calculation control unit 70 does not move the optical path changing unit 31 when obtaining a tomographic image. Interference light synthesized by the fiber coupler 34 is made into parallel light by a collimator lens 80, is divided by wavelength by a diffraction grating 81, and converges at a photodetector 83 by a condenser lens 82. Accordingly, spectrum interference fringes (power spectrums) are recorded on the photodetector 83. A Fourier transform relationship exists between the spectrum interference fringes and a correlation function. Therefore, by performing Fourier transform of the spectrum interference fringes obtained by the photodetector 83, a cross-correlation function between the measurement light and the reference light is obtained, and thus a shape in the Z-direction is obtained.

In the foregoing description, the measurement position of the two-dimensional tomographic image is set on the infrared front image or the visible front image, and the two-dimensional tomographic image is obtained by the OCT optical system 200 based on the set measurement position; however, it is not limited thereto. For example, a correspondence may be established between the three-dimensional tomographic image pre-obtained by the OCT optical system 200 and the visible front image. In this case, the calculation control unit 70 performs processing for obtaining the two-dimensional tomographic image corresponding to the set measurement position from the three-dimensional tomographic image. In other words, in the preferred embodiment, the obtainment of the two-dimensional tomographic image refers to the measurement (photographing) of the two-dimensional tomographic image after setting the measurement position and the obtainment of the two-dimensional tomographic image from the pre-obtained three-dimensional tomographic image.

For checking the measurement position of the two-dimensional tomographic image on the visible front image, which is obtained by setting the measurement position on the infrared front image, the calculation control unit 70, for example, obtains an observation image from the pre-obtained three-dimensional tomographic image and displays it on the monitor 75. This enables the measurement position to be set on the observation image. When the measurement position is set, the calculation control unit 70 obtains the two-dimensional tomographic image of the set measurement position from the three-dimensional tomographic image and displays it on the monitor 75. In addition, the calculation control unit 70 establishes a positional correspondence between the observation image and the visible front image, and displays a line indicating the measurement position of the two-dimensional tomographic image on the visible front image.

For setting the measurement position on the visible front image, the calculation control unit 70, for example, establishes a positional correspondence between the visible front image and the three-dimensional tomographic image and specifies the measurement position on the observation image. Then, the calculation control unit 70 obtains the two-dimensional tomographic image of the measurement position specified on the observation image and displays it on the monitor 75.

The observation images obtained from the three-dimensional tomographic image for establishing a correspondence to the visible front image include images such as a surface image and a two-dimensional tomographic image in the X-Y plane in a predetermined position in the Z-direction.

When photographing a visible front image of the fundus Ef by visible light with a predetermined wavelength, an image of a part corresponding to fundus tissue photographed by the visible light with the predetermined wavelength may be obtained from the three-dimensional tomographic image. For example, when photographing a visible front image of the fundus Ef by blue illumination light, a part in the vicinity of a nerve fiber layer of the fundus Ef is mainly photographed. Accordingly, it is sufficient that an image of a part corresponding to the nerve fiber layer of the fundus Ef is obtained from the three-dimensional tomographic image and a correspondence between the obtained image and the visible front image is established. In addition, when photographing a visible front image of the fundus Ef by red illumination light, deep tissue of the fundus Ef is mainly photographed. Accordingly, it is sufficient that an image of a part corresponding to the deep tissue of the fundus Ef is obtained from the three-dimensional tomographic image and a correspondence between the obtained image and the visible front image is established.

The invention claimed is:

1. An ophthalmic photographing apparatus for obtaining a tomographic image of a fundus of an examinee's eye by optical coherence tomography (OCT) using low coherent light, the apparatus comprising:
   an OCT optical system configured to obtain the tomographic image of the fundus including:
      an OCT light source;
      a splitter for splitting light emitted from the OCT light source into measurement light guided to a measurement optical path and reference light guided to a reference optical path;
      an optical scanner arranged in the measurement light path for scanning the light from the OCT light source on the fundus of the examinee's eye; and
      a photodetector for detecting light generated by synthesis of the measurement light reflected from the fundus and the reference light; and
   a calculation control unit configured:
      to obtain an OCT front image as a moving image with the use of the OCT optical system by two-dimensionally scanning the light from the OCT light source with the optical scanner and by detecting the light generated by synthesis of the measurement light and the reference light with the photodetector such that the OCT front image is generated based on an output signal from the photodetector, the OCT front image being a front image of the fundus;
      to display the OCT front image as the moving image obtained with the use of the OCT optical system on a monitor;
      to set a line on the OCT front image as the moving image such that the tomographic image of the fundus is obtained based on the line; and
      to obtain the tomographic image of the fundus corresponding to the line with the use of the OCT optical system by scanning light from the OCT light source with the optical scanner based on a scanning position corresponding to the set line and by detecting the light generated by synthesis of the measurement light and the reference light with the photodetector.

2. The ophthalmic photographing apparatus according to claim 1, wherein the OCT optical system is configured to provide the tomographic image of the fundus by detecting a spectrum of the light generated by synthesis of the measurement light and the reference light and by performing Fourier transform of the spectrum.

3. The ophthalmic photographing apparatus according to claim 1, wherein the apparatus further comprises a visible fundus photographing optical system for obtaining a visible front image of the fundus with visible light.

4. The ophthalmic photographing apparatus according to claim 3, wherein the calculation control unit displays the visible front image obtained with the use of the visible fundus photographing optical system and the tomographic image on the monitor and synthetically displays a measurement position of the tomographic image on the visible front image.

5. The ophthalmic photographing apparatus according to claim 3, wherein the calculation control unit establishes a correspondence between the OCT front image and the visible front image.

* * * * *